(12) United States Patent
Ganske et al.

(10) Patent No.: US 12,076,502 B2
(45) Date of Patent: Sep. 3, 2024

(54) BRAIDED CATHETER ASSEMBLIES

(71) Applicant: NorMedix, Inc., Eden Prairie, MN (US)

(72) Inventors: Karl V. Ganske, Hopkins, MN (US); Jeffrey M. Welch, Maple Grove, MN (US); Gregg Stuart Sutton, Maple Grove, MN (US)

(73) Assignee: NorMedix, Inc., Eden Prairie, MN (US)

( * ) Notice: Subject to any disclaimer, the term of this patent is extended or adjusted under 35 U.S.C. 154(b) by 111 days.

(21) Appl. No.: 16/889,188

(22) Filed: Jun. 1, 2020

(65) Prior Publication Data

US 2022/0331551 A1    Oct. 20, 2022

Related U.S. Application Data (63) Continuation of application No. 15/598,114, filed on May 17, 2017, now Pat. No. 10,702,674, which is a continuation-in-part of application No. 14/900,729, filed as application No. PCT/US2014/044519 on Jun. 27, 2014, now Pat. No. 9,937,321.

(60) Provisional application No. 62/338,491, filed on May 18, 2016, provisional application No. 61/840,764, filed on Jun. 28, 2013.

(51) Int. Cl.
    *A61M 25/00*    (2006.01)
(52) U.S. Cl.
    CPC ...... *A61M 25/005* (2013.01); *A61M 25/0041* (2013.01); *A61M 2025/0059* (2013.01)

(58) Field of Classification Search
    CPC .......... A61M 25/0045; A61M 25/0041; A61M 25/005; A61M 25/0105; A61M 25/0662; A61M 2025/0059
    See application file for complete search history.

(56) References Cited

U.S. PATENT DOCUMENTS

| | | |
|---|---|---|
| 5,938,587 A | 8/1999 | Taylor et al. |
| 5,951,539 A | 9/1999 | Nita et al. |
| | (Continued) | |

FOREIGN PATENT DOCUMENTS

| | | |
|---|---|---|
| CN | 1494441 A | 5/2004 |
| CN | 104936550 A | 9/2015 |
| | (Continued) | |

OTHER PUBLICATIONS

"U.S. Appl. No. 15/904,026, Examiner Interview Summary mailed Dec. 22, 2020", 3 pgs.

(Continued)

*Primary Examiner* — Jason E Flick
(74) *Attorney, Agent, or Firm* — Schwegman Lundberg & Woessner, P.A.

(57) ABSTRACT

A catheter assembly includes a catheter body extending from a catheter proximal portion to a catheter distal portion. The catheter body includes an inner liner and an outer sleeve. A braid assembly is within the catheter body and between the inner liner and the outer sleeve. The braid assembly includes a first filar array including one or more first filars helically extending around the catheter body in a first direction. The braid assembly further includes a second filar array including one or more second filars helically extending around the catheter body in a second direction opposed to the first direction.

16 Claims, 4 Drawing Sheets

(56) References Cited

U.S. PATENT DOCUMENTS

| | | | |
|---|---|---|---|
| 6,197,014 | B1 | 3/2001 | Samson et al. |
| 6,689,120 | B1 | 2/2004 | Gerdts |
| 8,317,772 | B2 | 11/2012 | Jansen et al. |
| 9,937,321 | B2 | 4/2018 | Welch |
| 10,702,674 | B2 | 7/2020 | Ganske et al. |
| 11,013,890 | B2 | 5/2021 | Welch et al. |
| 2010/0331936 | A1 | 12/2010 | Perrey et al. |
| 2011/0172698 | A1 | 7/2011 | Davies, Jr. et al. |
| 2013/0172851 | A1 | 7/2013 | Shimada et al. |
| 2013/0255866 | A1 | 10/2013 | Beckham |
| 2014/0142598 | A1 | 5/2014 | Fulton, III |
| 2014/0336572 | A1 | 11/2014 | Heisel et al. |
| 2014/0343537 | A1 | 11/2014 | Eversull et al. |
| 2016/0101261 | A1* | 4/2016 | Kugler ............... A61M 25/005 604/525 |
| 2016/0151605 | A1 | 6/2016 | Welch et al. |
| 2017/0095640 | A1* | 4/2017 | Rogers ............... A61M 25/005 |
| 2017/0252535 | A1 | 9/2017 | Ganske et al. |
| 2018/0243534 | A1 | 8/2018 | Welch et al. |
| 2023/0321397 | A1 | 10/2023 | Ganske et al. |

FOREIGN PATENT DOCUMENTS

| | | |
|---|---|---|
| CN | 105579091 | 5/2016 |
| CN | 109803710 | 5/2019 |
| CN | 114796796 A | 7/2022 |
| EP | 1068876 | 1/2001 |
| EP | 1567090 A1 | 8/2005 |
| EP | 3013404 | 4/2020 |
| JP | H08317986 | 12/1996 |
| JP | 2019520118 | 7/2019 |
| WO | 0110492 | 2/2001 |
| WO | 2001010492 | 2/2001 |
| WO | WO-2005065550 A2 | 7/2005 |
| WO | 2005072806 | 8/2005 |
| WO | 2013003835 | 1/2013 |
| WO | 2014189828 | 11/2014 |
| WO | 2014210427 | 12/2014 |
| WO | 2017201280 | 11/2017 |

OTHER PUBLICATIONS

"U.S. Appl. No. 15/904,026, Response filed Dec. 23, 2020 to Final Office Action mailed Aug. 6, 2020", 23 pgs.
"European Application Serial No. 17800166.5, Response filed Jan. 7, 2021 to Communication Pursuant to Article 94(3) EPC mailed Aug. 28, 2020", 8 pgs.
"U.S. Appl. No. 15/04,026, Notice of Allowance mailed Jan. 26, 2021", 9 pgs.
"Japanese Application Serial No. 2018-560834, Notification of Reasons for Refusal mailed Mar. 16, 2021", with English translation, 11 pages.
U.S. Appl. No. 14/900,729 U.S. Pat. No. 9,937,321, filed Dec. 22, 2015, Introducer Sheath for Radial Artery Access.
U.S. Appl. No. 15/904,026, filed Feb. 23, 2018, Introducer Sheath for Radial Artery Access.
U.S. Appl. No. 15/598,114 U.S. Pat. No. 10,702,674, filed May 17, 2017, Braided Catheter Assemblies.
"Chinese Application Serial No. 201780041148.1, Office Action mailed Jan. 6, 2021", with English translation, 28 pgs.
"Chinese Application Serial No. 201780041148.1, Response filed Jan. 18, 2022", with English claims, 21 pages.
"Chinese Application Serial No. 201780041148.1, Response filed Nov. 17, 2021 to Office Action mailed Sep. 2, 2021", with English claims, 11 pages.
"Chinese Application Serial No. 202210336351.4, Voluntary Amendment filed Nov. 18, 2022", with English translation of claims, 16 pgs.
"International Application Serial No. PCT/US2017/033319, Response filed Mar. 18, 2018 to Written Opinion mailed Aug. 16, 2017", 6 pgs.
"Mexican Application Serial No. MX/a/2018/014179, Office Action mailed Sep. 13, 2022", with machine translation, 14 pgs.
"International Application Serial No. PCT US2014 044519, International Search Report mailed Oct. 21, 2014", 4 pgs.
"International Application Serial No. PCT US2014 044519, Written Opinion mailed Oct. 21, 2014", 11 pgs.
"International Application Serial No. PCT US2014 044519, International Preliminary Report on Patentability mailed Jan. 7, 2016", 13 pgs.
"European Application Serial No. 14818501.0, Response filed Aug. 11, 2016 to Communication pursuant to Rules 161(1) and 162 EPC mailed Feb. 12, 2016", 7 pgs.
"European Application Serial No. 14818501.0, Extended European Search Report mailed Feb. 2, 2017", 11 pgs.
"U.S. Appl. No. 14/900,729, Non Final Office Action mailed May 31, 2017", 20 Pgs.
"International Application Serial No. PCT US2017 033319, International Search Report mailed Aug. 16, 2017", 2 pgs.
"International Application Serial No. PCT US2017 033319, Written Opinion mailed Aug. 16, 2017", 7 pgs.
"European Application Serial No. 14818501.0, Response filed Sep. 4, 2017 to Extended European Search Report mailed Feb. 2, 2017", 7 pgs.
"U.S. Appl. No. 14/900,729, Response filed on Oct. 2, 2017 to Non Final Office Action mailed May 31, 2017", 17 pgs.
"U.S. Appl. No. 14/900,729, Notice of Allowance mailed Nov. 16, 2017", 10 pgs.
"U.S. Appl. No. 14/900,729, Examiner Interview Summary filed Nov. 17, 2017", 1 pgs.
"International Application Serial No. PCT US2017 033319, International Preliminary Report on Patentability mailed May 3, 2018", 4 pgs.
"Chinese Application Serial No. 201480046445.1, Office Action mailed Jun. 5, 2018", with English translation, 12 pages.
"U.S. Appl. No. 15/904,026, Non Final Office Action mailed Nov. 15, 2018", 11 pgs.
"European Application Serial No. 14818501.0, Communication Pursuant to Article 94(3) EPC mailed Dec. 6, 2018", 7 pgs.
"Chinese Application Serial No. 201480046445.1, Response filed Dec. 20, 2018 to Office Action mailed Jun. 5, 2018", with English claims, 7 pages.
"Chinese Application Serial No. 201780041148.1, Notification on Correction of Deficiencies mailed Jan. 18, 2019", with English translation, 2 pages.
"Chinese Application Serial No. 201480046445.1, Office Action mailed Mar. 14, 2019", with English translation, 9 pages.
"European Application Serial No. 14818501.0, Response Filed Apr. 16, 2019 to Communication Pursuant to Article 94(3) EPC mailed Dec. 6, 2018", 10 pgs.
"Mexican Application Serial No. MX a 2018 014179, Office Action mailed May 6, 2019", with English translation, 22 pages.
"U.S. Appl. No. 15/904,026, Response filed May 15, 2019 to Non Final Office Action mailed Nov. 15, 2018", 9 pgs.
"Chinese Application Serial No. 201480046445.1, Response filed May 29, 2019 to Office Action mailed Mar. 14, 2019", with English claims, 15 pages.
"U.S. Appl. No. 15/598,114, Non Final Office Action mailed Jun. 25, 2019", 16 pgs.
"European Application Serial No. 17800166.5, Response filed Jul. 18, 2019 to Communication pursuant to Rule 161(1) and Rule 162 EPC mailed Jan. 8, 2019", 10 pgs.
"U.S. Appl. No. 15/904,026, Notice of Non-Compliant Amendment mailed Aug. 2, 2019", 3 pgs.
"Chinese Application Serial No. 201480046445.1, Office Action mailed Sep. 29, 2019", with English translation, 7 pages.
"U.S. Appl. No. 15/904,026, Response to Notice of Non-Compliant Amendment mailed Aug. 2, 2019 filed Nov. 4, 2019", 7 pgs.
"Chinese Application Serial No. 201480046445.1, Response filed Dec. 13, 2019 to Office Action mailed Sep. 29, 2019", with English claims, 15 pages.
"European Application Serial No. 17800166.5, Extended European Search Report mailed Jan. 3, 2020", 6 pgs.

(56) References Cited

OTHER PUBLICATIONS

"U.S. Appl. No. 15/598,114, Response filed Dec. 23, 2019 to Non Final Office Action mailed Jun. 25, 2019", 17 pgs.
"U.S. Appl. No. 15/904,026, Final Office Action mailed Feb. 3, 2020", 17 pgs.
"U.S. Appl. No. 15/598,114, Notice of Allowance mailed Apr. 8, 2020", 8 pgs.
"U.S. Appl. No. 15/904,026, Response filed Jul. 1, 2020 to Final Office Action mailed Feb. 3, 2020", 16 pgs.
"European Application Serial No. 17800166.5, Response filed Jul. 30, 2020 to Extended European Search Report mailed Jan. 3, 2020", 17 pgs.
"U.S. Appl. No. 15/904,026, Final Office Action mailed Aug. 6, 2020", 16 pgs.
"European Application Serial No. 17800166.5, Communication Pursuant to Article 94(3) EPC mailed Aug. 28, 2020", 4 pgs.
"Chinese Application Serial No. 201780041148.1, Response filed May 21, 2021 to Notification on Correction of Deficiencies mailed Jan. 18, 2019", with English claims, 26 pages.
"Chinese Application Serial No. 201780041148.1, Office Action mailed Sep. 2, 2021", with English translation, 27 pages.
"Japanese Application Serial No. 2018-560834, Response filed Sep. 16, 2021 to Notification of Reasons for Refusal mailed Mar. 16, 2021", with English claims, 12 pages.
U.S. Appl. No. 15/598,114, filed May 17, 2017, Braided Catheter Assemblies.
"European Application Serial No. 17800166.5, Communication Pursuant to Article 94(3) EPC mailed Feb. 15, 2023", 4 pgs.
"European Application Serial No. 17800166.5, Response filed May 26, 2023 to Communication Pursuant to Article 94(3) EPC mailed Feb. 15, 2023", 72 pgs.
"Mexican Application Serial No. MX/a/2018/014179, Office Action mailed Mar. 16, 2023", with machine translation, 12 pgs.
"Mexican Application Serial No. MX/a/2018/014179, Response filed May 24, 2023 to Office Action mailed Mar. 16, 2023", with machine translation, 9 pgs.
"Mexican Application Serial No. MX/a/2018/014179, Response filed Nov. 24, 2022 to Office Action mailed Sep. 13, 2022", with machine translation, 26 pgs.
"Chinese Application Serial No. 202210336351.4, Office Action mailed Jan. 23, 2024", w/English translation, 9 pgs.
"Chinese Application Serial No. 202210336351.4, Response filed May 23, 2024 to Office Action mailed Jan. 23, 2024", with machine translation, 18 pgs.

* cited by examiner

BRAIDED CATHETER ASSEMBLIES

CLAIM OF PRIORITY

This patent application is a continuation of U.S. patent application Ser. No. 15/598,114, filed May 17, 2017, which application is a continuation-in-part application and claims the benefit of priority to U.S. patent application Ser. No. 14/900,729, entitled "INTRODUCER SHEATH FOR RADIAL ARTERY ACCESS," filed on Dec. 22, 2015, issued on Apr. 10, 2018 as U.S. Pat. No. 9,937,321; which application is a 371 national stage application and claims priority to International Patent Application Serial No. PCT/US2014/044519, entitled "INTRODUCER SHEATH FOR RADIAL ARTERY ACCESS," filed on Jun. 27, 2014; which claims the benefit of priority to Provisional Patent Application Ser. No. 61/840,764, entitled. "INTRODUCER SHEATH FOR RADIAL ARTERY ACCESS." filed on Jun. 28, 2013; all of which are hereby incorporated by reference herein in their entireties.

U.S. patent application Ser. No. 15/598,114, filed May 17, 2017, also claims the benefit of priority of U.S. Provisional Patent Application Ser. No. 62/338,491, entitled "BRAIDED CATHETER ASSEMBLIES," filed on May 18, 2016, which is hereby incorporated by reference herein in its entirety.

TECHNICAL FIELD

This document pertains generally, but not by way of limitation, to catheters including instruments used in diagnostic or therapeutic procedures.

BACKGROUND

Introducer sheaths, guide catheters and the like are used for diagnostic and therapeutic procedures. Sheaths and guide catheters are used to guide other instruments including catheters into and through the vasculature to one or more locations of interest. Catheters are delivered through one or more of a sheath or guide catheter, and are optionally navigated with stylets, guidewires or the like through vasculature beyond the distal ends of the sheath or guide catheter. The sheaths and guide catheters are in some examples similarly navigated through the vasculature (e.g., with guidewires).

Delivery through various features of the vasculature including vessels, thrombus, plaques or the like is performed with manipulation of one or more of these catheters (including one of an introducer sheath, guide catheter, catheter or the like). Manipulation includes one or more of axial pushing of the catheter, for instance from the proximal catheter end toward the distal catheter end; lateral bending of the catheter (e.g., perpendicular to the longitudinal axis of the catheter) to navigate bends in the vasculature or other passage; and rotation of the catheter, for instance by rotation of the proximal catheter end to correspondingly rotate the distal catheter end.

Overview

The present inventors have recognized, among other things, that a problem to be solved can include minimizing kinking of a catheter while enhancing manipulation characteristics of the catheter including one or more of pushability, torqueability and flexibility. As a conventional catheter is made more flexible (e.g., able to bend and navigate turns in a passage or vessel) the catheter is often becomes more prone to kinking. Further, in some examples conventional catheters include braiding (e.g., polymer, nitinol, stainless steel or the like) to enhance torqueability. The inclusion of braiding in these examples often decreases the kink-resistance of the catheter. Catheter are made more kink-resistant in some examples by including one or more coils (e.g., one or more of nitinol, stainless steel coils or the like) in the catheter. The one or more coils increase the kink-resistance of the catheter but do not provide the torqueability available with braiding. Further still, combining coils and braiding increases the dimensions of the catheter and correspondingly consumes valuable space (e.g., lumen space) otherwise available for the delivery of fluids, catheters, instruments or the like through the catheter or placement of conductors, instruments or other features within the catheter.

The present subject matter can help provide a solution to these problems, such as by varying one or more characteristics of structural features of a catheter including the pairing of braided filars in various ratios, sizes and pitches (inverse of pics per inch), the inclusion of one or more coils with braiding and the like. In one example, the braid includes a first array (X) of filars braided in a left hand direction and a second array (Y) of filars braided in a right hand direction. The filar counts are varied (e.g., X:Y in an example base 16 filar count, 15:1, 14:2, 12:4, 10:6, 8:8, 6:10, 12:4, 14:2, 15:1 or the like) to provide the desired degree of torqueability to the catheter. In other examples, the dimensions of the filars for the first and second arrays of filars vary. For instance, the dimensions of the filars in the first filar array (X) are smaller (one or more of width and height) than the dimensions of the filars in the second filar array (Y). In one example, the dimensions of the filars for the filar array having the smaller number of filars are relatively larger than the dimensions of the filars for the filar array having the greater number of filars. For example, the increase in dimensions for the fewer filars can provide increased torqueability in one direction (e.g., left handed rotation) while the greater number of filars can provide increased torqueability in the opposed direction (e.g., right handed rotation).

Further, the proposed arrangement increases kink resistance of the catheter. As previously discussed, conventional braided catheters are (in some examples) relatively prone to kinking with respect to catheters including coils. A catheter including the braided filars described herein is also resistant to kinking. In one example, the braiding includes a smaller number of filars in the second filar array with the filars of the array having relatively larger dimensions (e.g., widths) relative to the dimensions of the second filar array. In some examples, the filars of the second filar array include at least widths an order of magnitude greater than the filars of the first filar array. The second filar array thereby provides a braided brace extending over and under the first filar array including the larger number of filars. The braided brace is anchored within the catheter, for instance with a reflowed outer sleeve. The braided brace (anchored in place within the catheter) structurally supports the first filar array and enhances maintenance of the first filar array in its wound configuration even while the catheter is deflected, for instance in tortuous vasculature. Stated another way, the braided brace (e.g., the second filar array) anchors the first filar array in place within the catheter and provides structural support to the braid to resist kinking. That is to say, the braided brace provides a support skeleton (cage, frame or the like) within the catheter body that is interlaced with the first filar array to minimize (e.g., eliminate or decrease) kinking otherwise present with the first filar array.

Optionally, the second filar array includes one or more filars having dimensions approaching or equaling those of a coil. That is to say, the braiding includes one or more braided coils as part of at least one of the filar arrays. The braided coil is another example of a braided brace that provides support to at least one of the filar arrays to enhance kink resistance while the opposed filar array enhances torqueability. Further, incorporation of filars having dimensions similar to those of a coil (e.g., at least one of the filar arrays includes a coil) minimizes the profile of the braiding relative to an assembly including a braid with the coil separately wound over or positioned beneath the braid.

Because the second filar array anchors the first filar array and provides structural support, in one example because of the larger dimensions of the second filar array filars (e.g., forming a braided brace), the pitch (or inversely the pics per inch or PPI) of the braid are readily adjusted to levels that otherwise make the catheter more prone to kinking. For instance, by increasing the pitch of the first filar array (e.g., to 45 degrees or more) torqueability of the catheter is increased. Conversely, the first filar array with the higher pitch (e.g., decreased PPI) is less kink-resistant. The second filar array, braided with the first filar array, structurally supports the first filar array and enhances the kink-resistance otherwise minimized by the first filar array. In effect the first filar array enhances the kink resistance for the braiding while the second filar array facilitates enhanced torqueability.

In another example one or more supplemental coils are included with the braid. As previously described, the inclusion of a coil in some examples undesirably consumes space in the catheter or alternately requires the catheter have a larger outer diameter to accommodate the supplemental components. The present subject matter can help provide a solution to this problem as well by using a guide recess provided by the braid, for instance a helical track formed along the braid by one of the first or second filar arrays. In one example, the second filar array as described above includes a smaller number of filars relative to the first filar array. Optionally, the second filar array includes larger dimensions to provide additional structural support to the braid while at the same time promoting torqueability in the 'weak' direction of the braid (e.g., the direction of winding for the limited number of filars in the first filar array). The helical track of the second filar array provides a guide recess that extends along the second filar array and is configured to receive (at least a portion of) the coil therein. Positioning of the coil within the guide recess minimizes the overall profile of the coil while the coil provides additional kink resistance to the catheter. In an example a catheter including the second filar array provides structural support to the first filar array and the additional coil cooperates with the second filar array to clamp the first filar array therebetween and further enhance the kink resistance of the catheter.

Optionally, a first coil is provided on the proximal face of the first filar array (e.g., within a first guide recess) and a second coil is provided on the distal face of the first filar array (within a second guide recess). Reflowing of a sleeve over the braid and coil assembly anchors the at least one coil in place within the guide recess. Further, because the guide recess minimizes the profile of the coil the sleeve readily covers and incorporates the coil with the catheter without requiring a relatively thicker sleeve.

This overview is intended to provide an overview of some of the subject matter of the present patent application. It is not intended to provide an exclusive or exhaustive explanation of the disclosure. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

While the technology is susceptible to various modifications and alternative forms, specifics thereof have been shown by way of example and drawings, and will be described in detail. It should be understood, however, that the application is not limited to the particular embodiments described. On the contrary, the application is to cover modifications, equivalents, and alternatives falling within the spirit and scope of the technology.

DETAILED DESCRIPTION

The embodiments of the present disclosure described herein are not intended to be exhaustive or to limit the disclosure to the precise forms disclosed in the following detailed description. Rather, the embodiments are chosen and described so that others skilled in the art can appreciate and understand the principles and practices of the present disclosure.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The catheter examples as described herein can solve the problems associated with current catheter technology by providing novel designs, construction and materials. The catheters, described herein, are optionally used in interventional procedures including access to one or more vessels or passages (e.g., arteries, veins, vessels, body passages or cavities and the like). Further, the catheters described herein facilitate enhanced deflection, torqueability and other mechanical characteristics of the catheter during navigation while at the same time minimizing kinking. For instance, where significant arterial tortuosity is encountered such with a radial artery access or a femoral approach on an obese patient, the catheters described herein are configured for navigation through such vessels. The catheters described herein include, but are not limited to, introducer sheaths, guide catheters, delivery catheters, or other typically tubular devices used in diagnostic or therapeutic procedures (e.g., including instruments, fluid delivery passages, balloons or the like).

In various embodiments, the catheters include a composite built tube fabricated using a wound metal inner layer (a braid assembly) and jacketed with layers of polymer inside and out, for instance an inner liner and outer sleeve, respectively. The metallic inner layer is constructed with a multi-filar (6-30 filars) helically wound braid structure. In some embodiments, the filars are swaged, such that one or more of the filars is partially flat or ovular (e.g., including rectangular) in cross-section to achieve a tight wire matrix. In other examples, the braid assembly is made with one or more non-swaged, round, square or rectangular filars (optionally in combination with other filars having the swaged configuration). As described herein, the braid assembly includes filar arrays, for instance first and second filar arrays that are helically wound and interlaced.

In various embodiments, the wall thickness of the braid assembly ranges from about 0.0005 to 0.020 inches thick. The braid assembly improves the mechanical integrity of the catheter, such as compared to current guide catheters with respect to kinking, buckling, flexibility, radial strength, and maintaining circularity of the catheter lumen cross-section. This improvement is achieved in one example by varying number of filars in each of the filar arrays (e.g., in various ratios including but not limited to, 15:1, 14:2, 13:3, 12:4, 11:5, 10:6, 9:7, 8:8, 7:9, 6:10, 5:11, 4:12.3:13, 2:14, 1:15 with a total filar count of 16 filars).

In another example, the improved mechanical characteristic (or characteristics) is achieved by varying dimensions (e.g., dimensions in cross section) of one or more of the filars in one or more of the arrays. For instance, in arrays with the ratio 14:2 the first filars (14 filars) include first filar dimensions in the cross section such as one or more of diameter, thickness or width less than corresponding dimensions of the second filars (2 filars). Stated another way, the second filars are fewer in number and are larger in at least one cross sectional dimension relative to the first filars. As described herein, the second filars structurally support the more narrow first filars in the manner of a braided brace, and thereby behave as a frame, skeleton, cage or the like that maintains the first filars in a desired configuration (e.g., without kinking or buckling during deflection). Optionally the second filars include one or more filars, such as coils, interlaced with the first filars. The coils act as a braided brace for the first filars similar to the second filars previously described. The first filars (and the second filars including the braided brace) provide improved torqueability to the catheter, while the braided brace structurally supports the braid assembly and provides at least enhanced kink resistance. The inclusion of a braided brace incorporates the profile of the brace into the braid assembly and thereby avoids coupling additional support structures over or beneath the braid assembly with attendant consumption of space (or enlargement of the catheter) avoided.

In still another example, the catheters described herein include a coil wound along the braid assembly, for instance in a guide recess provided by one of the filar arrays. The coil enhances the mechanical characteristics of the catheters. Optionally, the coil extends helically along one or more of the filars including for example the braided brace. The coil and the braided brace cooperate to capture and hold the first filars (described above) in place within the catheter. Further, infiltration of the outer sleeve (e.g., a reflowed or shrunk sleeve) into the braid assembly and the optional coils fixes each of the braided brace and the coil (optional) in place. The outer sleeve and the braided brace capture and hold the first filars in place and minimize (e.g., eliminate or decrease) kinking of the catheters. Where the coil is included along the braid assembly, the coil and the braided brace are captured within the outer sleeve (e.g., reflowed) and clamp the first filars therebetween. Kinking, buckling or the like of the first filars is thereby resisted by one or more of the braided brace or the coil in combination with the outer sleeve.

In at least some examples, the catheter of this disclosure also comprises an outer sleeve, such as an outer polymer layer and an inner liner, such as an inner polymer layer. In an embodiment, the outer polymer layer and the inner polymer layer include one or more polymers, such as PTFE, Pebax, or Polyurethane. The polymer layers are attached to the braid assembly by thermal polymer heat-shrinking or reflow. The wall thickness of the polymer layers ranges from 1.0 to 3.0 thousandths of an inch for each layer.

In various embodiments, the catheters include a pre-shaped curve, such as a curved distal end region. The catheter attains the pre-shaped curve configuration by, for instance, heat-setting the metal portion of the catheter where the curved configuration is specified. The curve retains its shape in body temperature and over time does not substantially soften (e.g., to unintentionally change shape). The guide catheter optionally includes a soft (low durometer) polymer distal tip, various distal curve shapes, a radiopaque distal marker band, a proximal luer adapter or the like.

The catheters described herein range in size from 3F to 34F and in lengths from at least 15 cm or more to 205 cm or less. As previously described, the features, elements and functions described herein as well as their equivalents are used in a variety of catheters including, but not limited to, introducer sheaths, guide catheters, catheters including one or more of instruments or delivery lumens, or the like. That is to say, the enhancements to each of torqueability, pushability, flexibility, kink-resistance or the like are readily applied to various catheter styles and types.

Figure 1:
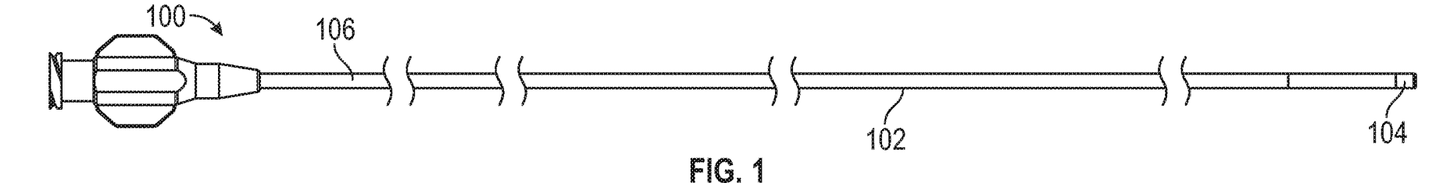
FIG. 1 is a front view of a catheter, according to an embodiment.
Figure 2:
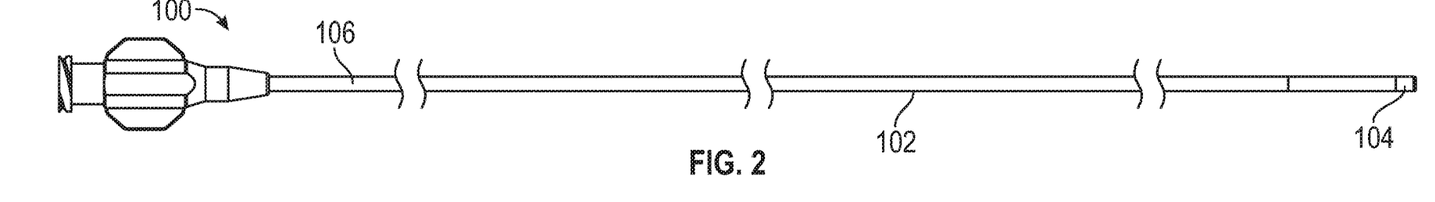
FIG. 2 is a back view of a catheter, according to an embodiment.
Figures 3, 4, 5:
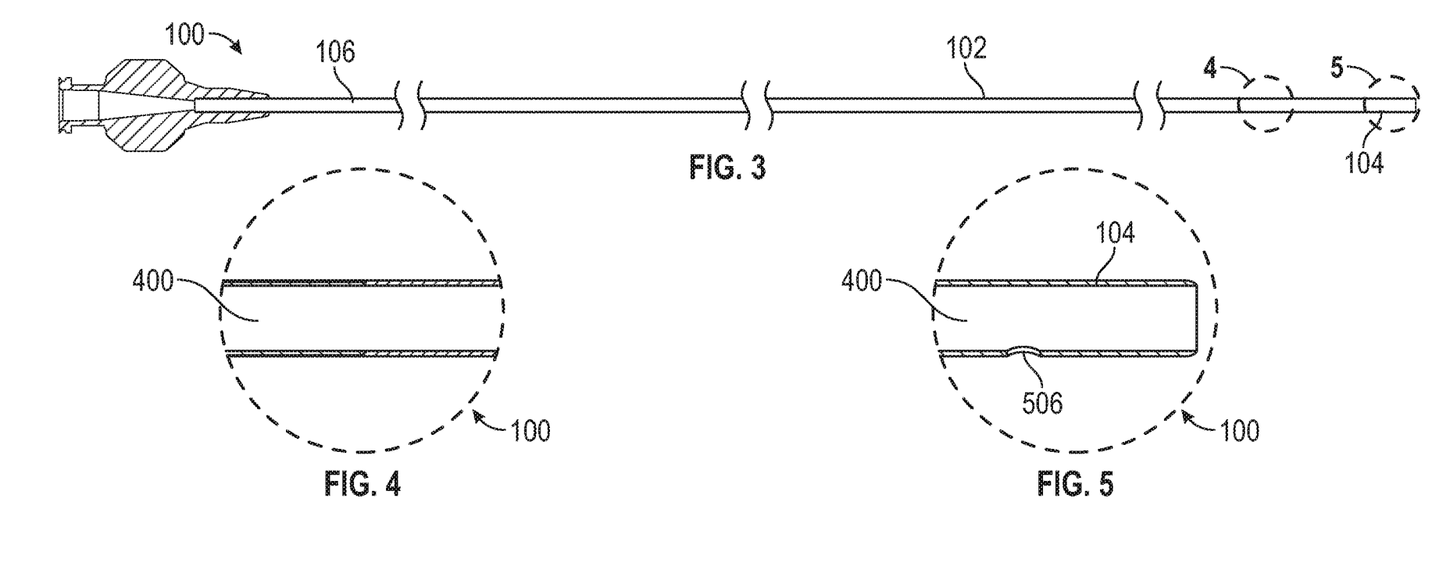
FIG. 3 is a cross-sectional view of a catheter, according to an embodiment.
FIG. 4 is a cross-sectional view of a portion of a catheter, according to an embodiment.
FIG. 5 is a cross-sectional view of a portion of a catheter, according to an embodiment.

In reference now to the Figures. FIG. 1 shows a front view of a guide catheter 100, according to an embodiment. FIG. 2 shows a back view of the guide catheter 100. FIG. 3 shows a cross-sectional view of the guide catheter 100 shown in FIGS. 1 and 2. In an embodiment, the guide catheter 100 can be configured for introducing interventional catheters into the vasculature of a patient.

In an embodiment, the catheter 100 includes a catheter body 102 (e.g., a main tubular shaft with an optional lumen) with a distal end portion (including a distal tip 104) and a proximal end portion (including a proximal end 106). The distal tip 104 is on the opposed end of the tubular shaft 102 from the proximal end 106. The distal tip 104 includes at least one layer of polymer. In another example, the distal tip 104 includes at least two layers of polymer. Optionally, the distal tip 104 includes an inner layer and an outer layer. In one example, the inner layer of the distal tip 104 includes PTFE. In another example, the outer layer of the distal tip 104 includes Pebax. In an embodiment, the distal tip 104 has a length of at least 0.05 inches. In another embodiment, the distal tip 104 has a length of at least 0.02 inches long. In yet another embodiment, the distal tip 104 is 0.2 inches long or shorter. In a further embodiment, the distal tip 104 can be is 0.5 inches long or less.

In various embodiments, the catheter body (e.g., including the tubular shaft 102) includes a main inner structural layer, for instance one or more of the braid assembly, discrete coil or combinations of the same as described herein. The main inner structural layer includes a helically interlaced braid assembly extending between the proximal end portion and the distal end portion (e.g., along the entire length or a portion of the length of the catheter body). In various embodiments, the braid assembly covers at least a portion of the inner liner of the catheter. The outer sleeve, for instance a shrink tube, reflowed polymer or the like surrounds the braid assembly and in at least some examples infiltrates interstitial spaces of the braid assembly (e.g., between filars, coils, opposed helixes of the braid or the like).

As described herein, the catheter body including the main tubular shaft 102 includes an outer layer (e.g., a jacket, such as an outer sleeve). The outer layer optionally includes a polymer. The outer layer surrounds the braid assembly (e.g., jackets, coats, covers or the like). The outer layer is fixed (e.g., fixedly coupled) to the braid assembly and optionally the inner liner through one or more of shrinking of the outer layer (shrink tubing) or infiltration of the braid assembly and optionally contacting the inner liner (by reflowing).

In various embodiments, the inner liner of the catheter (e.g., the catheter body including the main tubular shaft 102) includes a polymer. The inner layer (e.g., the inner liner) extends along and couples with an inner surface of the braid assembly (e.g., jackets, coat or covers or the like). The inner layer is coupled (e.g., fixedly coupled) to the main inner structural layer through one or more of compression of the braid assembly onto the liner (e.g., with an outer sleeve including a shrink tube), compression achieved during braiding of the braid assembly onto the liner, infiltration of the braid assembly by a reflowed outer sleeve including contact and coupling of the reflowed polymer with the inner liner.

Figure 10:
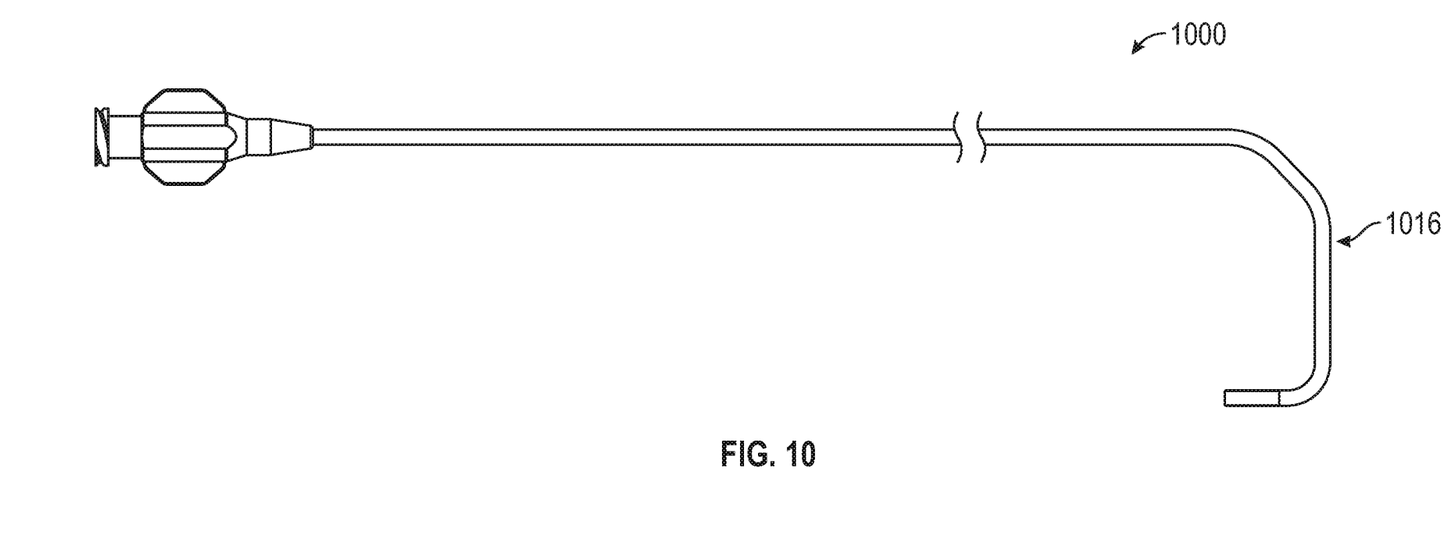
FIG. 10 is a front view of a catheter, according to an embodiment.

The main tubular shaft 102 optionally includes a curve, for instance at or near the distal end portion including the distal tip 104 (shown in FIG. 10). The curve shape is configured for anatomical conformance. The shape is optionally formed and heat processed into the main tubular shaft 102, such as in the braid assembly or another metal portion. In one example, the braid assembly terminates distally prior to the curve of the distal end portion.

In various embodiments, the braid assembly is laminated between the inner layer (inner liner) and the outer layer (outer sleeve), such that the lamination does not fuse the outer sleeve and the inner liner together.

In an embodiment, the catheter is at least 60 cm long and not longer than 200 cm. In another embodiment, the main tubular shaft 102 is at least 10 cm long and not longer than 300 cm. In still another embodiment, the main tubular shaft 102 is at least 30 cm long and not longer than 250 cm. In a further embodiment, the main tubular shaft 102 is at least 50 cm long and not longer than 225 cm.

In an embodiment, the main tubular shaft 102 includes an outer diameter of at least 0.060 inches and not more than 0.115 inches (e.g., the outer diameter of the outer sleeve when coupled with the remainder of the catheter body). In another embodiment, the main tubular shaft 102 includes an outer diameter of at least 0.060 inches. In a further embodiment, the main tubular shaft 102 includes an outer diameter of at least 0.040 inches. In yet another embodiment, the main tubular shaft 102 includes an outer diameter of at least 0.050 inches. In further embodiments, the main tubular shaft 102 includes an outer diameter of at least 0.070 inches, at least 0.080 inches or the like. In still another embodiment, the main tubular shaft 102 has an outer diameter of no greater than 0.115 inches. In further examples, the main tubular shaft 102 has an outer diameter including, but not limited to, no greater than 0.095 inches, no greater than 0.105 inches, no greater than 0.125 inches, no greater than 0.135 inches.

FIG. 4 and FIG. 5 show cross-section views of portions of a catheter 100, according to various embodiments. In the example shown, the catheter 100 includes an inner lumen 400. In other examples, the catheter is without an open inner lumen. FIG. 5 shows a cross-section of a portion of the distal tip 104. As seen in FIG. 5, the guide catheter 100 in an example includes one or more apertures 506. In various embodiments, the catheter body including the main tubular shaft 102 includes an aperture 506 extending from the interior of the catheter 100 to the exterior of the catheter. In an embodiment, the distal tip 104 includes the aperture 506.

Figure 6:
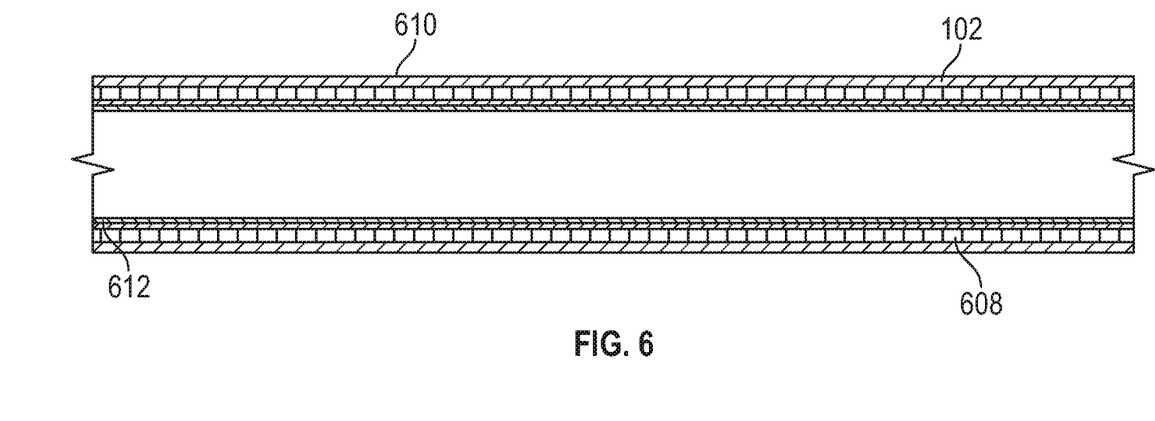
FIG. 6 is a cross-sectional view of a portion of a catheter, according to an embodiment.
Figure 7:
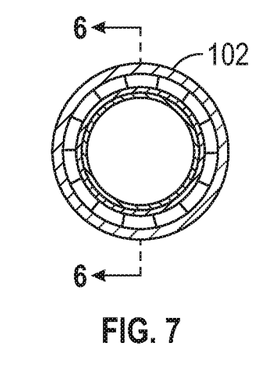
FIG. 7 is a cross-sectional view of a portion of a catheter, according to an embodiment.

FIG. 6 shows a cross-sectional view of a portion of the main tubular shaft 102 along the longitudinal axis of the catheter 100, according to an embodiment. FIG. 7 shows a cross-sectional view from the end of the main tubular shaft 102 (e.g., orthogonal to the longitudinal axis of the catheter 100). In an embodiment, the catheter body including the main tubular shaft 102 includes the braid assembly 608. The braid assembly 608 includes two or filar arrays interlaced in opposed (left and right) directions around the catheter body. As described herein, each of the filar arrays includes one or more filars including but not limited to flat or ovular (e.g., swaged) filars, coils (circular filars) or the like. In various embodiments, the braid assembly includes one or more filars constructed with, but not limited to, metal (stainless steel, Nitinol or the like), polymers, composites or combinations of filars constructed with two or more of the materials described herein.

In various embodiments, the braid assembly 608 filars are swaged. In various embodiments, the braid assembly component filars includes include between at least 2 and 30 filars having a picks per inch (inverse of pitch) of between 30 and 180. In various embodiments, the braid assembly includes at least 4 filars and not more than 24 filars. In other embodiments, the braid assembly includes at least 8 filars and not more than 16 filars. In various embodiments, the metallic filars of the braid assembly 608 include cross sectional shapes including, but not limited to, rectangular cross-sections, circular cross-sections, ovular cross-sections, elliptical cross-sections (another example of an oval) or the like. In various embodiments, the braid assembly 608 filars are coated, for instance with PTFE, prior to braiding into the interlaced configuration of the braid.

In an embodiment, the braid assembly 608 includes welded terminations. In an embodiment, the braid assembly 608 includes a distal end having a gold coating. In various embodiments, the gold coating ranges from about 0.5 mm to 2 mm thick. In other embodiments, the gold coating ranges from about 0.4 mm to 2.5 mm thick. In still other embodiments, the gold coating ranges from 0.25 mm to 3 mm thick.

In an embodiment, the braid assembly 608 includes thickness (e.g., from the braid assembly exterior to the braid assembly interior) that ranges from about 0.0015 inches to 0.010 inches. In another embodiment, the braid assembly 608 includes a thickness of at least 0.0010 inches. In still another embodiment, the braid assembly 608 includes a thickness of at least 0.0005 inches. In other embodiments, the main inner braid assembly 608 includes a thickness of no greater than 0.015 inches. In still other embodiments, the braid assembly 608 includes a thickness of no greater than 0.020 inches.

As described herein, the catheter body including the main tubular shaft 102 includes an outer layer 610, such as an outer sleeve. The outer layer 610 includes a polymer in at least one example. The outer layer 610 extends around (e.g., jackets, covers, coats or the like) at least a portion of the braid assembly 608. In an embodiment, the outer layer 610 is at least about 0.001 inches thick and not more than about 0.005 inches thick. In another embodiment, the outer layer 610 is least about 0.0007 inches thick. In still another embodiment, the outer layer 610 is at least about 0.0005 inches thick. In yet another embodiment, the outer layer 610 is no more than about 0.007 inches thick. In further embodiments, the outer layer is no more than about 0.01 inches thick.

Optionally, the outer layer 610 includes one or more of polymers including, but not limited to, Pebax, PTFE, shrink tubing or the like. In another example, the outer layer 610 includes nylon. In an embodiment, the outer layer 610 is coated with a hydrophilic polymer. In another example, the outer layer 610 includes at least two layers. Optionally, each of the two layers includes Pebax or one or more of the polymers described herein. In another example, the outer layer 610 is heat shrinkable to snugly couple form the outer layer 610 onto the braid assembly 608. In yet another example, the outer layer 610 includes a reflowable polymer that is heated and reflows around the braid assembly 608. Optionally, the reflowed outer layer 610 infiltrates and captures one or more of the filars (including the braided brace) within the outer layer 610. As described herein, the outer layer 610 in cooperation with the braided brace (e.g., a coil, filars as described herein or the like) and an optional discrete coil maintain the braid assembly 608 in a specified (unkinked) configuration even with significant deflection of the catheter 100 (relative to a braid assembly without the structural support described herein).

In an embodiment, the catheter body including the main tubular shaft 102 includes an inner liner, such as an inner layer 612. The inner layer 612 includes a polymer including, but not limited to, a lubricious polymer such as PTFE (e.g., to provide strength and facilitate passage of instruments through an optional center lumen as shown in FIGS. 6 and 7). The inner layer 612 extents along at least an interior portion of the braid assembly 608.

In an embodiment, the inner layer 612 is at least about 0.001 inches and not more than about 0.005 inches thick. In another embodiment, the inner layer 612 is at least about 0.0007 inches thick. In yet another embodiment, the inner layer 612 is at least about 0.0005 inches thick. In another example, the inner layer 612 is no more than about 0.007 inches thick. In still another example, the inner layer is no more than about 0.01 inches thick. Optionally, the inner layer 612 includes one or more polymers including, but not limited to, PTFE (described above), nylon, and coated polymers (e.g., coated with a hydrophilic polymer).

Figure 8:
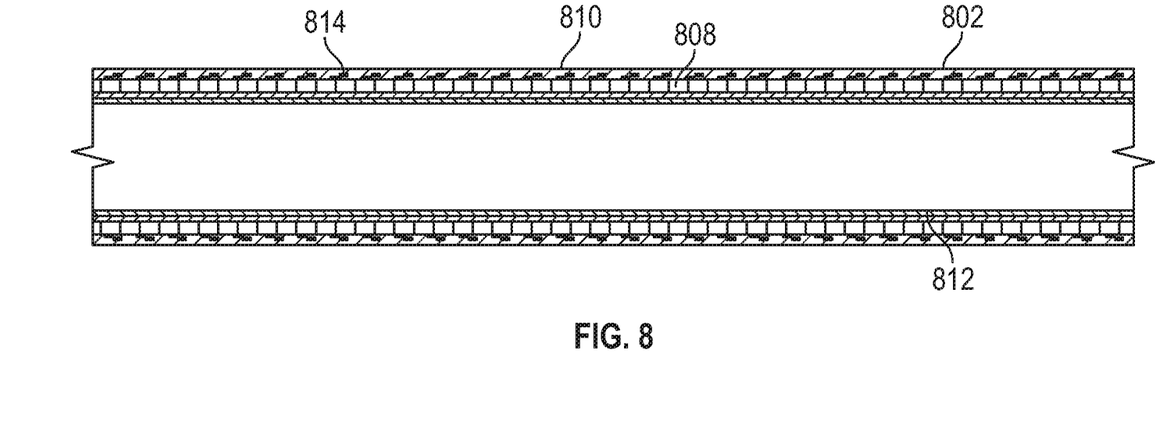
FIG. 8 is a cross-sectional view of a portion of a catheter, according to an embodiment.
Figure 9:
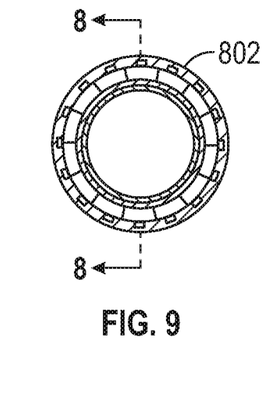
FIG. 9 is a cross-sectional view of a portion of a catheter, according to an embodiment.

In an embodiment, the outer layer 610 (outer sleeve) and the inner layer 612 (inner liner) are fused together, for instance through the braid assembly 608 (shown in FIGS. 6 and 8). FIG. 8 shows a cross-section view of a portion of a main tubular shaft 802 (a portion of the catheter body), according to an embodiment. FIG. 9 shows a cross-section view from the end of the main tubular shaft 802. In various embodiments, the main tubular shaft 802 include a braid assembly 814. The braid assembly 814 is disposed between an optional inner braid assembly 808 (or other structural support layer) and the outer layer 810. In another example, the braid assembly 814 is between the outer sleeve (e.g., outer layer 810) and the inner liner (e.g., inner layer 812). In yet another example, the braid assembly 814 is disposed within a portion of the outer layer 810. The braid assembly 814 covers at least a portion of the optional inner braid assembly 808 in another example.

In an embodiment, the filars of the braid assembly 814 includes metal or a polymer including, but not limited to, stainless steel. Nitinol or the like. In one embodiment, the braid assembly 814 is at least about 0.0005 inches thick and not more than about 0.010 inches thick. In another embodiment, the braid assembly 814 is at least about 0.005 inches thick and not more than about 0.010 inches thick. In still another embodiment, the braid assembly 814 is at least about 0.0004 inches thick. In a further embodiment, the braid assembly 814 is at least about 0.0003 inches thick. In other embodiments, the braid assembly 814 no more than about 0.015 inches thick, no more than about 0.020 inches thick or the like.

FIG. 10 shows a front view of an example guide catheter 1000 according to an embodiment. The guide catheter 1000 includes a distal end curve 1016. The distal end curve 1016 is, in one example, configured for anatomical conformance. As described herein, the distal end curve 1016 is heat processed and formed of a formable portion of the catheter 1000, for instance in regions including one or more of the braid assemblies described herein, a separate metal feature or the like. The distal end curve 1016 retains its shape in body temperature and over time does not substantially soften and unspecified shape changes of the curve are thereby prevented.

The catheters described herein include a catheter body including a braid assembly having at least first and second interlaced filar arrays, with each of the filar arrays including one or more respective first and second filars extending in opposed helixes. The braid assembly is between an inner liner and an outer sleeve. In at least one example, the braid assembly including interstitial spaces between filars, filar arrays and the like, is infiltrated by the outer sleeve.

Figure 11:
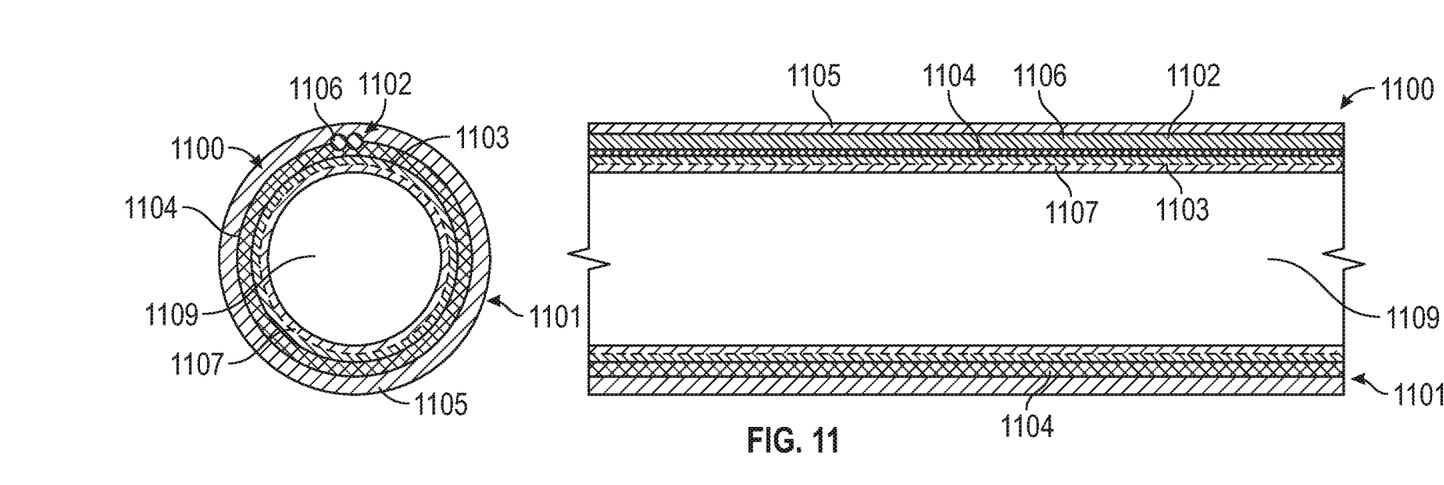
FIG. 11 is a composite cross sectional view of one example catheter taken along a longitudinal axis (right view) and an orthogonal axis (left view).

The braid assembly is constructed with a multi-filar (e.g., 6-30 filars) helically wound interlaced braid structure. In some embodiments, the filars are swaged, such that one or more of the filars is partially flat or ovular (e.g., including rectangular and elliptical) in cross-section to achieve a tight wire matrix. In other examples, the braid assembly is made with one or more non-swaged, round, square or rectangular filars (optionally in combination with other filars having the swaged configuration). In one example, the one or more filars one or both of the first and second filar arrays include filars approximating the dimensions and characteristics of a coil (e.g., a circular or ovular cross section, material characteristics such as Young's modulus, flexural modulus or the like). One example of a braided brace 1102 is shown in FIG. 11 by the circular (coil) filars as part of the braid assembly 1100 (and shown in the cross-sectional view on the right taken along the longitudinal axis of the catheter).

Figure 12:
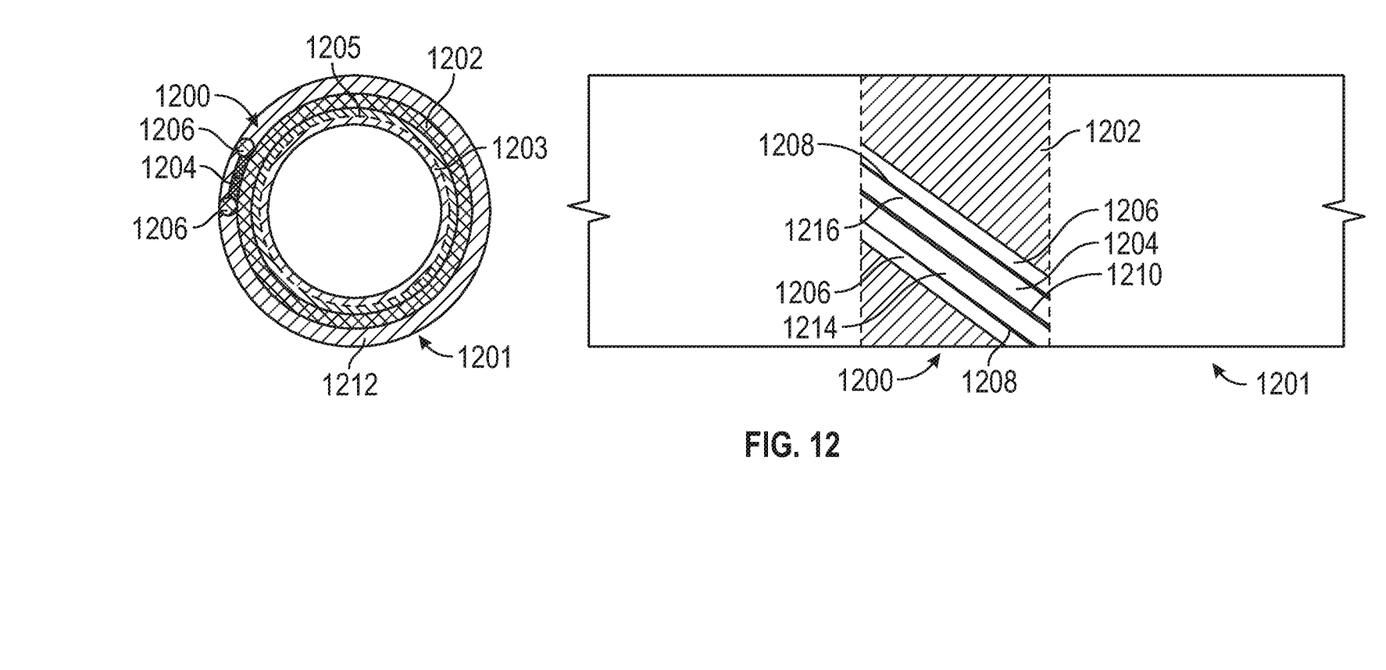
FIG. 12 is a composite sectional view of another example catheter having a partial section along a longitudinal axis (right view) and a cross section along an orthogonal axis (left view).

In various embodiments, the wall thickness of the braid assembly 1100 ranges from about 0.0005 to 0.020 inches thick. The braid assembly 1100 improves the mechanical characteristics of the catheter 1101, such as compared to current guide catheters with respect to kinking, buckling, flexibility, radial strength, and maintaining circularity of the catheter lumen 1109 cross-section. The braid assembly 1100 of the catheter also improves characteristics of the catheter including, but not limited to, one or more torqueability, flexibility, pushability or kink resistance. This improvement is achieved in one example by varying number of filars (e.g., filars, coils or the like) in each of the filar arrays 1104, 1106 (e.g., in various ratios including but not limited to, 15:1, 14:2, 13:3, 12:4, 11:5, 10:6, 9:7, 8:8.7:9, 6:10, 5:11, 4:12, 3:13, 2:14, 1:15 with a total filar count of 16 filars). One example of a braid assembly 1200 including an unbalanced ratio is shown in FIG. 12 that includes a 16 filar count example braid having 14 first filars in the first filar array 1202 and 2 second filars in the second filar array 1204. For illustration purposes interlacing is removed (but present in the braid assembly).

In another example, the one or more improved mechanical characteristics are achieved by varying dimensions (e.g., dimensions in cross section) of one or more of the filars in one or more of the arrays. For instance, in arrays with the ratio 14:2 the first filars (14 filars of a first filar array) include first filar dimensions in the cross section such as one or more of diameter, thickness or width less than corresponding dimensions of the second filars (2 filars of a second filar array). Stated another way, the second filars are fewer in number and are larger in at least one cross sectional dimension relative to the first filars. The second filars structurally support the more narrow first filars in the manner of a braided brace, and thereby provide a frame, skeleton, cage or the like that maintains the first filars in a desired configuration (e.g., without kinking or buckling during deflection). One example of a braid assembly 1200 including filars having different dimensions between the first and second filar arrays 1202, 1204 is shown in FIG. 12. As shown the second filars (e.g., coils, filars or the like) of the second filar array 1204 have at least one larger dimension relative to the first filars of the first filar array 1202. In one example, the second filars have a dimension, such as width, at least one order of magnitude larger than the first filars.

Optionally, the second filars include one or more filars, such as coils, interlaced with the first filars. An example of second filars including coils (including filars having coil shapes and dimensions) is provided in FIG. 11. Although a single array 1106 of second filars is shown in FIG. 11, other examples include multiple arrays of the second filars interlaced with a corresponding number of first filar arrays 1104. The one or more interlaced coils are another example of a braided brace for the first filars. The first filars (and the second filars including the braided brace 1102) provide improved torqueability to the catheter, while the braided brace 1102 structurally supports the braid assembly 1100 and provides enhanced kink resistance (and optionally other improved characteristics including pushability and torqueability). The inclusion of a braided brace 1102 incorporates the profile of the brace into the braid assembly and thereby minimizes the inclusion of additional support structures (such as coils) over or beneath the braid assembly with attendant consumption of space (or enlargement of the catheter) avoided.

In still another example, the catheters described herein include a coil 1206 wound along the braid assembly 1200, for instance in a guide recess 1208 provided by one of the filar arrays 1202, 1204. One example of discrete coils is shown in FIG. 12 by the one or more coils 1206 extending along the second filar array 1204. The coil 1206 enhances the mechanical characteristics of the catheter 1201. Optionally, the coil 1206 extends helically along one or more of the filars including for example the braided brace 1210. The coil 1206 and the braided brace 1210 cooperate to capture and hold the first filars (described above) 1202 in place within the catheter 1201. Further, infiltration of the outer sleeve 1212 (e.g., a reflowed or shrunk sleeve) into the braid assembly 1200 and the optional coils 1206 fixes each of the braided brace 1210 and the coil 1206 (optional) in place. The outer sleeve 1212 and the braided brace 1210 capture and hold the first filars 1202 in place and minimize (e.g., eliminate or decrease) kinking of the catheter 1201. Where the coil 1206 is included along the braid assembly 1200, the coil and the braided brace are captured within the outer sleeve 1212 (e.g., reflowed) and clamp the first filars 1202 therebetween. Kinking, buckling or the like of the first filars is thereby resisted by one or more of the braided brace 1210 or the coil 1206 in combination with the outer sleeve 1212.

As further shown in FIG. 12, the catheter 1201 further includes one or more guide recesses 1208 adjacent to the second filar array 1204. The one or more faces 1214, 1216 of the second filar array 1204 form the guide recesses 1208. For instance, as shown in FIG. 12, the second filar array 1204 includes proximal and distal faces 1214, 1216. The one or more guide recesses 1208 follow the helical track of one of the filar arrays 1202, 1204 (in the example shown the second array 1204) and optionally include two guide recesses, one along the proximal face 1214 and the other along the distal face 1216 of the second filar array 1204. Because the second filar array 1204 is interlaced with the first filar array 1202 to form the braid assembly 1200 proximal and distal faces 1214, 1216 are present where the second filar array 1204 is on the exterior of the braid assembly (e.g., between passes of the first filars of the first filar array 1202). In at least those zones, the coil (or coils) 1206 is partially received within the braid assembly 1200 to thereby minimize the space (e.g., outer sleeve 1212 thickness) used to contain the coils 1206 in the outer sleeve. In one example, the braid assembly 1200 facilitates the inclusion of a discrete coil 1206 and the benefits to the mechanical characteristics (e.g., kink-resistance or the like) while minimizing the space needed to retain the coil 1206 in the catheter 1201. At least a portion of the profile of the coils 1206 is concealed within the guide recesses 1208 while the remainder is within the outer layer 1212. The outer layer 1212 is in one example made thinner with its exterior immediately adjacent to the outer surface of the (recessed) coils.

As previously described herein one or more of the ratio of filars, dimensions of filars and components included with the braid assembly 1100, 1200 and along the braid assembly are varied to provide specified mechanical characteristics for a catheter 1101, 1201. For instance, various ratios and dimensions of filars are used to provide a specified torqueability for the catheter 1101, 1201 and at the same time enhance kink-resistance. One or more optional discrete coils 1206 are optionally provided along the braid assembly 1100, 1200, for instance within guide recesses 1208 of the braid assembly 1200, to further enhance the mechanical characteristics of the catheter. Tables 1, 2 and 3 provided herein describe each of the various features of an example braid assembly including, but not limited to, filar ratios between first and second filar arrays, filar dimensions, filar shapes, discrete coils and positioning of the same. These features are chosen and implemented in the catheter to provide the specified characteristics for a therapeutic or diagnostic procedure.

Table 1 (below) provides one example of a braid assembly including a filar count of 16 total filars. As shown, the ratios between the first and second filar arrays, and in some examples their cross sectional shapes, are varied between each of the example braid configurations. Although the smaller filar arrays (e.g., six and under) include the option for circular filars (e.g., coils or the like), circular filars are also included in some examples with filar array having larger filar counts, for instance greater than six filars.

TABLE 1

Structural Braid Configuration (example of 16 filar count between arrays, but total filar count is higher or lower in examples such as 6, 6, 10, 12, 14, 18, 20, 22, 24, 26, 28, 30 or the like)

| Braid Configuration | First Filar Array-Filar Count (e.g., left hand helix) | First Filar Array-Filar Shape | Second Filar Array-Filar Count (e.g., right hand helix) | Second Filar Array-Filar Shape |
|---|---|---|---|---|
| X1 | 15 | flat or ovular | 1 | circular (e.g., coil); flat or ovular |
| X2 | 14 | flat or ovular | 2 | circular (e.g., coil); flat or ovular |
| X3 | 13 | flat or ovular | 3 | circular (e.g., coil); flat or ovular |
| X4 | 12 | flat or ovular | 4 | circular (e.g., coil); flat or ovular |
| X5 | 11 | flat or ovular | 5 | circular (e.g., coil); flat or ovular |
| X6 | 10 | flat or ovular | 6 | circular (e.g., coil); flat or ovular |
| X7 | 9 | flat or ovular | 7 | flat or ovular |
| X8 | 8 | flat or ovular | 8 | flat or ovular |
| X9 | 7 | flat or ovular | 9 | flat or ovular |
| X10 | 6 | circular (e.g., coil); flat or ovular | 10 | flat or ovular |
| X11 | 5 | circular (e.g., coil); flat or ovular | 11 | flat or ovular |
| X12 | 4 | circular (e.g., coil); flat or ovular | 12 | flat or ovular |
| X13 | 3 | circular (e.g., coil); flat or ovular | 13 | flat or ovular |
| X14 | 2 | circular (e.g., coil); flat or ovular | 14 | flat or ovular |
| X15 | 1 | circular (e.g., coil); flat or ovular | 15 | flat or ovular |

Table 2 describes filar configurations including dimensions for each of the first and second filar arrays. In some examples, larger filar dimensions (e.g., of the second filar array) are paired with smaller filar dimensions of the other filar array (e.g., the first filar array). Examples of filars having circular cross sections are also provided including dimensions between about 0.001 to 0.01 inches. Table 2 further qualitatively shows the relative difference between dimensions of the first and second filar arrays in the Order of Magnitude column. As shown, at least some the filar configurations provide one or more of the filars of one array as at least one order of magnitude larger in a dimension, such as width or diameter, relative to the corresponding dimension of the other filars of the other (e.g., second) filar array.

TABLE 2

Filar Configurations (example flat/ovular or coil dimensions used in some examples with the braid configurations of Table 1)

| Filar Configuration | First Filar Array-Filar Shape | First Filar Array-Filar Dimensions (inches) | Second Filar Array-Filar Shape | Second Filar Array-Filar Dimensions (inches) | Order of Magnitude Difference (e.g., of width in diameter) |
|---|---|---|---|---|---|
| Y1 | flat or ovular | 0.0005 × 0.003 | flat or ovular | 0.002 × 0.015 | Yes |
| Y2 | flat or ovular | 0.0005 × 0.003 | flat or ovular | 0.002 × 0.010 | Yes |
| Y3 | flat or ovular | 0.002 × 0.015 | flat or ovular | 0.002 × 0.015 | No |
| Y4 | flat or ovular | 0.002 × 0.015 | circular (e.g., coil) | 0.001 | No |
| Y5 | flat or ovular | 0.002 × 0.015 | circular (e.g., coil) | 0.003 | No |
| Y6 | flat or ovular | 0.0005 × 0.003 | circular (e.g., coil) | 0.004 | Yes |
| Y7 | flat or ovular | 0.0005 × 0.003 | circular (e.g., coil) | 0.005 | Yes |
| Y8 | flat or ovular | 0.0005 × 0.003 | circular (e.g., coil) | 0.008 | Yes |
| Y9 | flat or ovular | 0.0005 × 0.003 | circular (e.g., coil) | 0.01 | Yes (2 orders of magnitude) |

Table 2 provides an array of example dimensions. Filar Dimensions (flat or ovular) vary between thicknesses of 0.0005 to 0.005 and widths of 0.001 to 0.030
As described herein, in one example, a filar array with fewer filars has relatively larger filar dimensions relative to a companion filar array having a greater number of filars Table 3 describes the placement of one or more discrete coils with the braid assembly. Further, the table describes options for positioning of the coils within guide recesses, for instance along the one or more guide recesses 1208 previously shown in FIG. 12 and provided alongside one of the filar arrays, for instance the second filar array 1204 having larger dimensions and correspondingly larger recesses (e.g., having a depth corresponding to the thickness or diameter of the second filars). In various examples, one or more coils are positioned within proximal or distal guide recesses 1208 (e.g., along the proximal or distal faces 1214, 1216 of a filar assembly such as the second filar assembly).

TABLE 3

Discrete Coil (example coils optionally used in some examples with the braid configurations of Tables 1 and 2)

| Coil Configuration | Placement of Coil Relative to Braid (Exterior or Interior) | Coil Positioning in Braid Guide Recess or Recesses | Proximal or Distal Guide Recess (Relative to braid filar or filars providing guide recesses) | Number of Coils |
|---|---|---|---|---|
| Z1 | Exterior | Yes | Proximal | 1 |
| Z2 | Exterior | Yes | Proximal and Distal | 2 |

TABLE 3-continued

Discrete Coil (example coils optionally used in some examples with the braid configurations of Tables 1 and 2)

| Coil Configuration | Placement of Coil Relative to Braid (Exterior or Interior) | Coil Positioning in Braid Guide Recess or Recesses | Proximal or Distal Guide Recess (Relative to braid filar or filars providing guide recesses) | Number of Coils |
|---|---|---|---|---|
| Z3 | Exterior | Yes | Distal | 1 |
| Z4 | Exterior | No | NA | 1 |
| Z5 | Exterior | No | NA | 2 |
| Z6 | Interior | No | NA | 1 |
| Z7 | Interior | No | NA | 2 |

Coil Dimensions: Various including 0.001 to 0.010 inches.

A variety of prophetic example catheter configurations are provided herein. The configurations are drawn by assembling one or more of the configurations provided in Tables 1, 2 and 3 and provide variation in mechanical characteristics based on the configurations chosen (e.g., the inclusion of a braided brace, such as larger filars in one of the arrays, a coil or the like improve kink-resistance).

The catheter of example 1 includes a braid assembly provided over a PTFE inner liner with an intermediate tie layer provided between the PTFE and the braid assembly (e.g., to facilitate coupling of the braid assembly and optionally an outer sleeve with the inner liner). The inner liner has an outer diameter of about 0.255 to 0.256 inches; the tie layer outer diameter (over the inner liner) is about 0.260 to 0.2605 inches; and the braid assembly outer diameter (over the tie layer) is about 0.270 to 0.271 inches. An outer sleeve, such as Pebax or the like, is provided along the catheter and over the braid assembly.

The catheter of example 2 includes a braid assembly with a discrete coil extending along the braid assembly exterior. The braid assembly includes an 8:8 ratio of first filars to second filars. In one example, the first filars have cross sectional dimensions of about 0.002 (thickness) by about 0.015 (width) inches. The second filars have the same dimensions. In another example, the second filars have the previously described dimensions (e.g., 0.002×0.015 inches) while the first filars have cross sectional dimensions of about 0.0005 inches by 0.003 inches. In this example, the second filars have dimensions an order of magnitude greater than the first filars. The braid assembly is provided over a PTFE inner liner with an intermediate tie layer. The inner liner has an outer diameter of about 0.2555 to 0.2565 inches; the tie layer outer diameter (over the inner liner) is about 0.2585 to 0.259 inches; and the braid assembly outer diameter (over the tie layer) is about 0.261 to 0.2615 inches. The coil is loaded over the braid assembly and retained therealong with the outer sleeve, such as Pebax or the like. In one example, the outer sleeve has a durometer of 55D and an outer diameter of between about 0.280 inches to 0.285 inches. Optionally, an end of the coil is fixed near the corresponding end of the braid assembly and the coil is wound around the braid assembly in the same direction (e.g., from proximal to distal). In another example, the coil is would along one or more guide recesses of one of the filar arrays as described herein.

The catheter of example 3 includes a braid assembly having an 8:8 ratio of eight filars for the first filar array and eight filars for the second filar array. The braid assembly is provided over a PTFE inner liner and an intermediate tie layer is provided between the PTFE and the braid assembly (e.g., to facilitate coupling of the braid assembly and optionally an outer sleeve with the inner liner). The inner liner has an outer diameter of about 0.255 to 0.266 inches; the tie layer outer diameter is about 0.258 to 0.259 inches; and the braid assembly outer diameter is about 0.263 to 0.264 inches. The first filars have cross sectional dimensions of 0.0005 (thickness) by 0.003 (width) inches. The second filars have cross section dimensions of 0.002 (thickness) by 0.015 (width) inches. The second filars have dimensions an order of magnitude greater than the first filars. The braid assembly is braided at 50 picks per inch, and is encapsulated with a polymer having a durometer of 55D and an outer diameter of about 0.280 to 0.285 inches.

In other examples (related to example 3), the braid assembly has a 14:2 or 12:4 ratio with the first filars having the same dimensions. In this example, the picks per inch are optionally increased (e.g., greater than 50, for instance to 180 PPI). In still another example, the braid assembly has a 15:1 ratio of first filars to second filars. Each of the first and second filars include the same dimensions as those for the 8:8 example provided immediately above.

In either of the examples (e.g., ratios of 8:8, 14:2, 12:4, 15:1) the catheter optionally includes a discrete coil. For instance, in the last example including the 15:1 ratio the coil is positioned within a guide recess formed along the second filar array (e.g., including the single second filar). The guide recess appears in the examples as one or more rifled grooves extending along the braid assembly. In addition to providing increased kink-resistance, the inclusion of the coil enhances the radial strength of the catheter (resistance to collapsing).

The catheter of example 4 includes a braid assembly having a 14:2 ratio of fourteen first filars for the first filar array and two second filars for the second filar array. In a similar manner to the previous examples, the braid assembly is provided over a PTFE inner liner (e.g., inner sleeve 1107 in FIG. 11 and inner sleeve 1203 in FIG. 12) and an intermediate tie layer (e.g., 1103, 1205, respectively) is provided between the PTFE and the braid assembly. The inner liner has an outer diameter of about 0.255 to 0.256 inches; the tie layer outer diameter is about 0.258 to 0.259 inches; and the braid assembly outer diameter is about 0.263 to 0.2635 inches. The first filars have cross sectional dimensions of 0.0005 (thickness) by 0.003 (width) inches. The second filars have cross section dimensions of 0.002 (thickness) by 0.015 (width) inches and are an order of magnitude greater than the first filars. Optionally, the two filars of the second filar array are staggered 180 degrees apart (e.g., on opposite sides of the catheter) to form a double helix. The braid assembly is braided at 90 PPI, and is encapsulated with a polymer (e.g., outer sleeve 1105) having a durometer of 55D and an outer diameter of about 0.280 to 0.285 inches.

The catheter of example 5 includes a braid assembly having a 15:1 ratio of fifteen first filars for the first filar array and one second filar for the second filar array. The filars are provided at 160 PPI. In a similar manner to the previous examples, the braid assembly is provided over a PTFE inner liner and an intermediate tie layer is provided between the PTFE and the braid assembly. The inner liner has an outer diameter of about 0.2555 to 0.256 inches; the tie layer outer diameter is about 0.258 to 0.259 inches; and the braid assembly outer diameter is about 0.2625 to 0.2635 inches. The first filars have cross sectional dimensions of 0.0005 (thickness) by 0.003 (width) inches. The second filar has cross sectional dimensions of 0.002 (thickness) by 0.015 (width) inches and is an order of magnitude greater than the first filars.

The second filar array in this example provides at least one guide recess (e.g., along the proximal or distal faces of the filar array) and a coil is wound along the filar array and positioned within the guide recess (the recess serves as a guide for placement of the coil). The coil is at least partially received within the guide recess and the profile of the coil is thereby decreased because it is partially absorbed by the filar array and its guide recess. In one example, where the coil is wound in a particular direction (e.g., left hand) the second filar array is also wound left handed (and the first filar array wound right handed) to ensure placement of the coil within the guide recess.

The braid assembly and the coil are encapsulated with a polymer (outer sleeve) having a durometer of 55D and an outer diameter of about 0.280 to 0.285 inches. Optionally, the outer sleeve is reflowed multiple time (e.g., at least twice) to remove gas bubbles in the sleeve. The catheter of example 5 has enhanced radial strength and flexibility relative to at least some of the other examples.

Example 6 includes a selection of catheters including braid assemblies having ratios of 15:1, 14:2, 12:4 and so on. The braid assemblies include second filars having dimensions approaching or equaling those of a coil. For instance, filar (coil) diameters of about 0.003 to 0.005 inches (e.g., larger than the 0.002×0.015 filars described herein). The second filars of the second filar array are interlaced with the first filar array. In one example, the second filars are staggered around the catheter body, for instance according to the count of the second filars (4 second filars at 90 degree intervals, 3 at 120 degree intervals, 2 at 180 degree intervals or the like). Optionally, these catheters and the second filar arrays of each are paired with discrete coils that are positioned within one or more guide recesses of the second filar array.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this technology pertains. All publications and patent applications are herein incorporated by reference to the same extent as if each individual publication or patent application was specifically and individually indicated by reference.

The technology has been described with reference to various specific and preferred embodiments and techniques. However, it should be understood that many variations and modifications may be made while remaining within the spirit and scope of the technology.

Various Notes & Examples

Example 1 can include subject matter such as can include a catheter assembly comprising: a catheter body extending from a catheter proximal portion to a catheter distal portion, the catheter body includes: an inner liner, and an outer sleeve; and a braid assembly within the catheter body and between the inner liner and the outer sleeve, the braid assembly includes: a first filar array including one or more first filars helically extending around the catheter body in a first direction, and a braided brace interlaced with the first filar array, the braided brace extends around the catheter body in a second direction opposed to the first direction, wherein the braided brace anchors and supports the first filar array.

Example 2 can include, or can optionally be combined with the subject matter of Example 1, to optionally include wherein the braided brace includes a second filar array including one of more second filars.

Example 3 can include, or can optionally be combined with the subject matter of one or any combination of Examples 1 or 2 to optionally include wherein the one or more second filars have a second filar width greater than a first filar width of the one or more first filars.

Example 4 can include, or can optionally be combined with the subject matter of one or any combination of Examples 1-3 to optionally include wherein the second filar width is at least one order of magnitude greater than the first filar width.

Example 5 can include, or can optionally be combined with the subject matter of one or any combination of Examples 1-4 to optionally include wherein second filar array includes fewer second filars than the first filars of the first filar array.

Example 6 can include, or can optionally be combined with the subject matter of Examples 1-5 to optionally include wherein the braided brace includes a coil interlaced with the first filar array.

Example 7 can include, or can optionally be combined with the subject matter of Examples 1-6 to optionally include wherein the coil includes a circular cross section.

Example 8 can include, or can optionally be combined with the subject matter of Examples 1-7 to optionally include wherein the outer sleeve is reflowed over the braid assembly, and the reflowed outer sleeve anchors the braided brace within the catheter body, and the reflowed outer sleeve and the braided brace cooperate to structurally support the first filar array.

Example 9 can include, or can optionally be combined with the subject matter of Examples 1-8 to optionally include wherein the braid assembly includes a torqueable and kink-resistant braid assembly, the first filar array includes a first torqueability and a first kink-resistance, and the braided brace includes a second kink resistance greater than the first kink resistance.

Example 10 can include, or can optionally be combined with the subject matter of Examples 1-9 to optionally include wherein the braided brace includes a second torqueability less than the first torqueability of the first filar array.

Example 11 can include, or can optionally be combined with the subject matter of Examples 1-10 to optionally include a coil extending helically along an exterior of the braid assembly.

Example 12 can include, or can optionally be combined with the subject matter of Examples 1-11 to optionally include wherein the braided brace includes at least one guide recess extending helically around the catheter body, and the coil is received in the at least one guide recess.

Example 13 can include, or can optionally be combined with the subject matter of Examples 1-12 to optionally include wherein the at least one guide recess extends along one of a proximal face or a distal face of the braided brace.

Example 14 can include, or can optionally be combined with the subject matter of Examples 1-13 to optionally include wherein the coil and the braided brace clamp the braid assembly therebetween.

Example 15 can include, or can optionally be combined with the subject matter of Examples 1-14 to optionally include a catheter assembly comprising: a catheter body extending from a catheter proximal portion to a catheter distal portion, the catheter body includes an inner liner, and an outer sleeve; a braid assembly within the catheter body and between the inner liner and the outer sleeve, the braid assembly includes: a first filar array including one or more first filars helically extending around the catheter body in a first direction, a second filar array including one or more second filars helically extending around the catheter body in a second direction opposed to the first direction, and wherein at least one of the first or second filar arrays includes at least one guide recess helically extending with the first or second filars; and a coil is received in the at least one guide recess and extends helically around the catheter body with the first or second filars.

Example 16 can include, or can optionally be combined with the subject matter of Examples 1-15 to optionally include wherein the one or more second filars of the second filar array have a larger dimension across a filar cross section than a smaller dimension of the one or more first filars of the first filar array.

Example 17 can include, or can optionally be combined with the subject matter of Examples 1-16 to optionally include wherein the at least one guide recess extends along the second filar array including the larger dimension, and the at least one guide recess includes a recess depth varying proportionally with the larger dimension.

Example 18 can include, or can optionally be combined with the subject matter of Examples 1-17 to optionally include wherein the one or more second filars include flat or ovular filars and the larger dimension includes one or more of width and thickness of the flat or ovular filars.

Example 19 can include, or can optionally be combined with the subject matter of Examples 1-18 to optionally include wherein the one or more second filars include circular filars and the larger dimension includes a diameter of the circular filars.

Example 20 can include, or can optionally be combined with the subject matter of Examples 1-19 to optionally include wherein the coil includes a coil profile, and at least a first portion of the coil profile is received within the at least one guide recess.

Example 21 can include, or can optionally be combined with the subject matter of Examples 1-20 to optionally include wherein the coil profile includes a second portion of the coil profile, and the second portion of the coil profile is received in the outer sleeve.

Example 22 can include, or can optionally be combined with the subject matter of Examples 1-21 to optionally include wherein the coil includes a coil profile, and at least a portion of the coil profile is received within the at least one guide recess and coextensive with a braid profile of the braid assembly.

Example 23 can include, or can optionally be combined with the subject matter of Examples 1-22 to optionally include wherein the coil includes a diameter of about 0.001 to 0.010 inches.

Example 24 can include, or can optionally be combined with the subject matter of Examples 1-23 to optionally include wherein at least one of the first or second filar arrays includes: a proximal guide recess extending along a proximal face of the first or second filar array, and a distal guide recess extending along a distal face of the first or second filar array.

Example 25 can include, or can optionally be combined with the subject matter of Examples 1-24 to optionally include wherein the coil is received in one of the proximal or distal guide recesses.

Example 26 can include, or can optionally be combined with the subject matter of Examples 1-25 to optionally include wherein the coil includes a first coil and a second coil, and the first coil is received in the proximal guide recess and the second coil is received in the distal guide recess.

Example 27 can include, or can optionally be combined with the subject matter of Examples 1-26 to optionally include wherein the coil extends over an exterior of the braid assembly.

Example 28 can include, or can optionally be combined with the subject matter of Examples 1-27 to optionally include wherein the coil extends over an interior of the braid assembly.

Example 29 can include, or can optionally be combined with the subject matter of Examples 1-28 to optionally include a catheter assembly comprising: a catheter body extending from a catheter proximal portion to a catheter distal portion, the catheter body includes: an inner liner, and an outer sleeve; and a braid assembly within the catheter body and between the inner liner and the outer sleeve, the braid assembly includes: a first filar array including one or more first filars helically extending around the catheter body in a first direction, and a second filar array including one or more second filars helically extending around the catheter body in a second direction opposed to the first direction.

Example 30 can include, or can optionally be combined with the subject matter of Examples 1-29 to optionally include wherein a first filar count of the one or more first filars is greater than a second filar count of the one or more second filars.

Example 31 can include, or can optionally be combined with the subject matter of Examples 1-30 to optionally include wherein at least a second filar width of the one or more second filars is greater than a first filar width of the one or more first filars according to the difference between the first and second filar counts.

Example 32 can include, or can optionally be combined with the subject matter of Examples 1-31 to optionally include wherein at least a second filar width of the one or more second filars is greater than a first filar width of the one or more first filars when the first filar count is greater than the second filar count.

Example 33 can include, or can optionally be combined with the subject matter of Examples 1-32 to optionally include wherein a first filar count of the one or more first filars and the second filar count of the one or more second filars are at ratios including 15:1, 14:2, 13:3, 12:4, 11:5, 10:6.9:7, 8:8, 7:9, 6:10, 5:11.4:12, 3:13, 2:14, 1:15.

Example 34 can include, or can optionally be combined with the subject matter of Examples 1-33 to optionally include wherein at least a second filar width of the one or more second filars is greater than a first filar width of the one or more first filars.

Example 35 can include, or can optionally be combined with the subject matter of Examples 1-34 to optionally include wherein the second filar width is at least an order of magnitude greater than the first filar width.

Example 36 can include, or can optionally be combined with the subject matter of Examples 1-35 to optionally include wherein at least one of the first and second filars includes a flat or ovular cross section.

Example 37 can include, or can optionally be combined with the subject matter of Examples 1-36 to optionally include wherein at least one of the first and second filars include a thickness dimension of about 0.0005 to 0.005 inches and a width dimension of about 0.001 to 0.030 inches.

Example 38 can include, or can optionally be combined with the subject matter of Examples 1-37 to optionally include wherein the braid assembly includes at least one guide recess extending along one of the first or second filar arrays, and comprising a coil received within the at least one guide recess.

Example 39 can include, or can optionally be combined with the subject matter of Examples 1-38 to optionally include wherein the coil follows a helix of either of the first or second filar arrays according the at least one guide recess extending the either of the first second filar arrays.

Example 40 can include, or can optionally be combined with the subject matter of Examples 1-39 to optionally include wherein the coil includes a coil profile, and at least a portion of the coil profile is positioned in the at least one guide recess.

Example 41 can include, or can optionally be combined with the subject matter of Examples 1-40 to optionally include wherein the coil includes a coil profile, and at least a portion of the coil profile is coextensive with a braid profile of the braid assembly.

Example 42 can include, or can optionally be combined with the subject matter of Examples 1-41 to optionally include wherein the coil includes a diameter of about 0.001 to 0.010 inches.

Example 43 can include, or can optionally be combined with the subject matter of Examples 1-42 to optionally include wherein at least one of the first or second filars of the first or second filar arrays is a coil interlaced with the other of the second or first filar arrays.

Example 44 can include, or can optionally be combined with the subject matter of Examples 1-43 to optionally include wherein the coil includes a diameter of about 0.001 to 0.010 inches.

Example 45 can include, or can optionally be combined with the subject matter of Examples 1-44 to optionally include wherein at least one of the first or second filar arrays includes a braided brace interlaced with the other of the second or first filar arrays.

Example 46 can include, or can optionally be combined with the subject matter of Examples 1-45 to optionally include wherein the outer sleeve is reflowed over the braid assembly, and the reflowed outer sleeve anchors the braided brace within the catheter body, and the reflowed outer sleeve and the braided brace of the first or second filar array cooperate to structurally support the other of the second or first filar array.

Example 47 can include, or can optionally be combined with the subject matter of Examples 1-46 to optionally include wherein the one or more first filars and the one or more second filars have a picks per inch (PPI) of between 30 and 180.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the disclosure should be determined with The claimed invention is:

1. A catheter assembly comprising:
a catheter body extending from a catheter proximal portion to a catheter distal portion, the catheter body includes:
an inner liner; and
an outer sleeve; and
a braid assembly within the catheter body and between the inner liner and the outer sleeve, the braid assembly includes:
a first filar array helically extending around the catheter body in a first direction, the first filar array including one or more first filars having a first profile, the first profile including one or more of a width or a height of each of the one or more first filars; and
a second filar array helically extending around the catheter body in a second direction opposed to the first direction, the second filar array including two or more second filars interlaced with the first filar array, wherein at least one of the two or more second filars includes a second profile having one or more of a width or a height greater than the respective width or height of the first profile, and wherein at least another filar of the two or more second filars includes the first profile.

2. The catheter assembly of claim 1, wherein the braid assembly is layered over the inner liner, and the outer sleeve is layered over the braid assembly.

3. The catheter assembly of claim 1, wherein the second profile width is at least one order of magnitude greater than the first profile width.

4. The catheter assembly of claim 1, wherein the second filar array includes less second filars than the first filars of the first filar array.

5. The catheter assembly of claim 1, wherein the first filar array includes a first kink-resistance; and
the second filar array includes a second kink resistance greater than the first kink resistance.

6. The catheter assembly of claim 1 comprising a coil extending helically along an exterior of the braid assembly.

7. The catheter assembly of claim 6, wherein one or more of the first or second filar arrays include at least one guide recess extending helically around the catheter body, and the coil is received in the at least one guide recess.

8. The catheter assembly of claim 1, wherein the one or more second filars of the second filar array include a coil.

9. A catheter assembly comprising:
a catheter body extending from a catheter proximal portion to a catheter distal portion, the catheter body includes:
an inner liner; and
an outer sleeve; and
a braid assembly within the catheter body and between the inner liner and the outer sleeve, the braid assembly includes:
a first filar array helically extending around the catheter body in a first direction, the first filar array including two or more first filars, wherein at least one of the two or more first filars includes a first profile and at least another first filar of the two or more first filars includes a second profile, wherein the first and second profiles each include respective width and height dimensions, and one or both of the width or height of the second profile is greater than the respective width or height of the first profile; and
a second filar array helically extending around the catheter body in a second direction, the second filar array including two or more second filars interlaced with the first filar array, wherein at least one second filar of the two or more second filars includes the width and height dimensions of the first profile and at least another second filar of the two or more second filars includes the width and height dimensions of the second profile.

10. The catheter assembly of claim 9, wherein the braid assembly is layered over the inner liner, and the outer sleeve is layered over the braid assembly.

11. The catheter assembly of claim 9, wherein the second profile width is at least one order of magnitude greater than the first profile width.

12. The catheter assembly of claim 9, wherein the second filar array includes fewer second filars than the first filars of the first filar array.

13. The catheter assembly of claim 9, wherein the first filar array includes a first kink-resistance; and
the second filar array includes a second kink resistance greater than the first kink resistance.

14. The catheter assembly of claim 9, wherein the two or more second filars of the second filar array include a coil.

15. The catheter assembly of claim 9 comprising a coil extending helically along an exterior of the braid assembly.

16. The catheter assembly of claim 15, wherein one or more of the first or second filar arrays include at least one guide recess extending helically around the catheter body, and the coil is received in the at least one guide recess.

* * * * *